United States Patent
Nishizawa et al.

(10) Patent No.: US 8,569,524 B2
(45) Date of Patent: Oct. 29, 2013

(54) BIS(TETRAHYDROFURAN) COMPOUND, METHOD FOR PRODUCTION OF THE COMPUND, AND USE OF THE COMPOUND

(75) Inventors: Mugio Nishizawa, Tokushima (JP); Yoshiyasu Fukuyama, Tokushima (JP); Hiroshi Imagawa, Tokushima (JP)

(73) Assignee: Glytech Inc., Kyoto-shi (JP)

( * ) Notice: Subject to any disclaimer, the term of this patent is extended or adjusted under 35 U.S.C. 154(b) by 811 days.

(21) Appl. No.: 12/529,500

(22) PCT Filed: Feb. 28, 2008

(86) PCT No.: PCT/JP2008/053519
§ 371 (c)(1),
(2), (4) Date: Dec. 22, 2009

(87) PCT Pub. No.: WO2008/105495
PCT Pub. Date: Sep. 4, 2008

(65) Prior Publication Data
US 2010/0105931 A1 Apr. 29, 2010

(30) Foreign Application Priority Data
Mar. 1, 2007 (JP) .................. 2007-51664

(51) Int. Cl.
C07D 493/00 (2006.01)
(52) U.S. Cl.
USPC ........................................ 549/464
(58) Field of Classification Search
USPC .......................................... 549/464
See application file for complete search history.

(56) References Cited

FOREIGN PATENT DOCUMENTS

| JP | 55-156583 | 12/1980 |
| JP | 3-86822 | 4/1991 |
| JP | 9-151132 | 6/1997 |

OTHER PUBLICATIONS

Y. Fukuyama, et al., "Rearranged Vibsane-Type Diterpenes from *Viburnum awabuki* and Photochemical Reaction of Vibsanin B", *Chem. Pharm. Bull.*, 2005, vol. 53, No. 1. pp. 72-80, particularly, p. 80, 16.

(Continued)

*Primary Examiner* — Taylor Victor Oh
(74) *Attorney, Agent, or Firm* — Kratz, Quintos & Hanson, LLP

(57) ABSTRACT

The present invention provides a new bis(tetrahydrofuran) compound having an excellent neurotrophic factor activity-enhancing effect, and a process for producing the same. The bis(tetrahydrofuran) compound of the present invention is represented by formula (1):

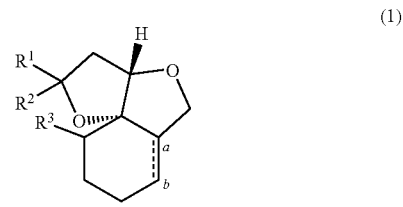

(1)

wherein $R^1$ and $R^2$ are the same or different, and represent a $C_{1-4}$ alkyl group, a $C_{1-5}$ alkoxy group, an aryl $C_{1-5}$ alkoxy group, a $C_{2-5}$ alkenyloxy group, or an aryl $C_{2-5}$ alkenyloxy group, or $R^1$ and $R^2$ together represent =O or =CH$_2$; $R^3$ represents a hydrogen atom or a group —CH$_2$—O—R$^4$; $R^4$ represents a $C_{1-4}$ alkyl group, a $C_{1-5}$ alkylcarbonyl group, or an aryl $C_{1-4}$ alkyl group that may have a substituent on an aryl ring; and a carbon-carbon bond between "a" and "b" represents a single bond or a double bond. The bis(tetrahydrofuran) compound has an excellent neurotrophic factor activity-enhancing effect.

8 Claims, 5 Drawing Sheets

(56) References Cited

OTHER PUBLICATIONS

Y. Fukuyama, et al., "Chemistry and Biological Activity of Vibsane-type Diterpenes", *Journal of Synthetic Organic Chemistry*, Japan, Jun. 1, 2007, vol. 65, No. 6, pp. 585-597, particularly, paragraph of 6.

International Search Report dated Apr. 22, 2008.

Y. Fukuyama, et al.; "Chemical and Biological Activity of Vibsane-type Diterpenes;" Journal of Synthetic Organic Chemistry; Jun. 1, 2007; vol. 65; No. 6; p. 585.

BIS(TETRAHYDROFURAN) COMPOUND, METHOD FOR PRODUCTION OF THE COMPUND, AND USE OF THE COMPOUND

TECHNICAL FIELD

The present invention relates to a bis(tetrahydrofuran) compound, a process for producing the same, and a use of the compound.

BACKGROUND ART

Along with the arrival of an aging society, senile dementia such as Alzheimer's-type dementia, dementia with Lewy bodies, Parkinson's disease, etc. has become a serious social issue.

The onset mechanism of these types of dementia has yet to be fully determined. However, a remarkable degeneration of cholinergic neurons is found in patients with Alzheimer's-type dementia, and the degeneration and loss of midbrain dopaminergic neurons are found in patients with Parkinson's disease. Such degeneration and loss are believed to cause the onset of dementia.

Neurotrophic factors (NTF) is a generic term for substances that promote the survival, differentiation, and regeneration of nerve cells. Specifically, these substances are high molecular proteins such as nerve growth factor (NGF), brain-derived neurotrophic factor (BDNF), neurotrophin 3 (NT-3), etc. NGF acts on cholinergic neurons, and BDNF acts on both cholinergic neurons and midbrain dopaminergic neurons. If the activities of these neurotrophic factors are successfully enhanced, such enhancement is likely to produce effective prevention or treatment of the above-described dementia.

Patent Document 1 discloses the use of one of the components of Compositae plants, i.e., helioxanthin, as an agent to enhance the activity of a cell differentiation inducing factor.

However, an effective preventive or treatment agent for patients with senile dementia, whose number is expected to increase, has not yet been developed.

Patent Document 1: Japanese Unexamined Patent Publication No. H9-151132

DISCLOSURE OF THE INVENTION

Technical Problem

An object of the present invention is to provide a new bis(tetrahydrofuran) compound having an excellent neurotrophic factor activity-enhancing effect, and a process for producing the bis(tetrahydrofuran) compound.

Technical Solution

The present inventors conducted intensive studies in an attempt to solve the above-described problem, and found that a bis(tetrahydrofuran) compound synthesized for the first time by the present inventors has an excellent neurotrophic factor activity-enhancing effect. The present invention has been completed based on such finding.

As shown in the following items 1 to 10, the present invention provides a bis(tetrahydrofuran) compound, a process for producing the same, and a neurotrophic factor activity enhancer containing the compound or a composition for ameliorating neurological disease containing the compound. Item 1. A bis(tetrahydrofuran) compound represented by formula (1):

[Chem. 1]

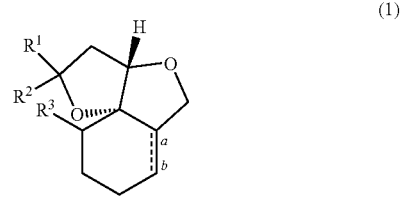

(1)

wherein $R^1$ and $R^2$ are the same or different, and represent a $C_{1-4}$ alkyl group, a $C_{1-5}$ alkoxy group, an aryl $C_{1-5}$ alkoxy group, a $C_{2-5}$ alkenyloxy group, or an aryl $C_{2-5}$ alkenyloxy group, or $R^1$ and $R^2$ together represent =O or =CH$_2$; $R^3$ represents a hydrogen atom or a group —CH$_2$—O—R$^4$; $R^4$ represents a $C_{1-4}$ alkyl group, a $C_{1-5}$ alkylcarbonyl group, or an aryl $C_{1-4}$ alkyl group optionally having one or more substituents on the aryl ring; and a carbon-carbon bond between "a" and "b" represents a single bond or a double bond.

Item 2. The bis(tetrahydrofuran) compound according to Item 1, wherein $R^1$ and $R^2$ together represent =O in formula (1).

Item 3. The bis(tetrahydrofuran) compound according to Item 1, wherein $R^1$ and $R^2$ together represent =CH$_2$ in formula (1).

Item 4. The bis(tetrahydrofuran) compound according to Item 1, wherein $R^1$ represents a $C_{1-4}$ alkyl group, and $R^2$ represents a $C_{1-5}$ alkoxy group, an aryl $C_{1-5}$ alkoxy group, a $C_{2-5}$ alkenyloxy group, or an aryl $C_{2-5}$ alkenyloxy group.

Item 5. A process for producing the bis(tetrahydrofuran) compound of Item 2, comprising reacting an acrylic acid compound represented by the following formula (2) with a quaternary ammonium fluoride:

[Chem. 2]

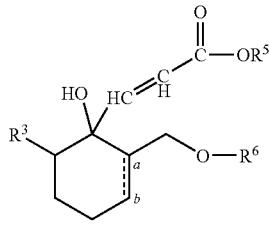

(2)

wherein $R^3$ and a carbon-carbon bond between "a" and "b" are as defined above; $R^5$ represents a $C_{1-4}$ alkyl group; and $R^6$ represents a silyl-based protecting group.

Item 6. A process for producing the bis(tetrahydrofuran) compound of Item 3, comprising reacting the bis(tetrahydrofuran) compound of Item 2 with Tebbe's reagent.

Item 7. A process for producing the bis(tetrahydrofuran) compound of Item 4, comprising reacting the bis(tetrahydrofuran) compound of Item 3 in an alcohol in the presence of an acid catalyst.

Item 8. A neurotrophic factor activity enhancer containing the bis(tetrahydrofuran) compound of Item 1.

Item 9. The activity enhancer according to Item 8, wherein the neurotrophic factor is a nerve growth factor or a brain-derived neurotrophic factor.

Item 10. A composition for ameliorating neurological disease, the composition containing the bis(tetrahydrofuran) compound of Item 1.

Advantageous Effects of the Invention

Bis(tetrahydrofuran) compounds represented by formula (1) of the present invention have an excellent neurotrophic factor activity-enhancing effect, and thus can be suitably used for the prevention or treatment of neurodegenerative diseases such as senile dementia commonly known as Alzheimer's disease, Down syndrome, Parkinson's disease, Creutzfeldt-Jakob disease, amyotrophic lateral sclerosis (ALS), and diabetic neuropathy; diseases caused by neurological disorders such as mental disorders including depression and schizophrenia; neurological disorders caused by sequelae of encephalitis, cerebral palsy, and head and/or spinal cord injuries; and cerebral vascular disorders associated with cerebral infarction, intracerebral bleeding, and cerebral arteriosclerosis. Among the bis(tetrahydrofuran) compounds represented by formula (1), bis(tetrahydrofuran) compounds represented by formulae (1C) and (1D) are particularly excellent in exhibiting the above effects.

The production process of the present invention can provide a new bis(tetrahydrofuran) compound as described above that has an excellent neurotrophic factor activity-enhancing effect.

Bis(tetrahydrofuran) compounds represented by formulae (1A) and (1B) of the present invention are useful intermediates for producing the bis(tetrahydrofuran) compounds represented by formulae (1C) and (1D).

DESCRIPTION OF EMBODIMENTS

Figure 1:
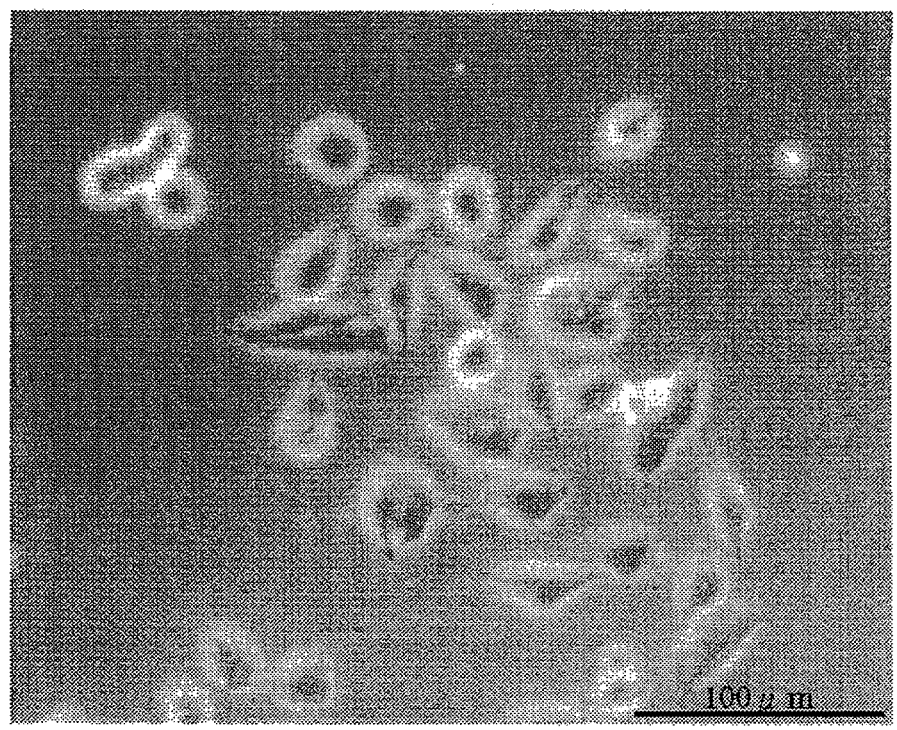
FIG. 1 is a micrograph showing cells cultivated in a medium containing DMSO.

Examples of $C_{1-4}$ alkyl groups represented by $R_1$, $R^2$, and $R^4$ in formula (1) include straight- or branched-chain alkyl groups having 1 to 4 carbon atoms, such as methyl, ethyl, n-propyl, isopropyl, n-butyl, sec-butyl, tert-butyl, etc., with methyl, ethyl, and n-butyl being preferable, and methyl being particularly preferable.

Examples of $C_{1-5}$ alkoxy groups represented by $R^1$ and $R^2$ in formula (1) include straight- or branched-chain alkoxy groups having 1 to 5 carbon atoms, such as methoxy, ethoxy, isopropoxy, tert-butoxy, prenyl (3-methyl-2-butenyl), etc., with methoxy and ethoxy being preferable, and ethoxy being particularly preferable.

Examples of aryl $C_{1-5}$ alkoxy groups represented by $R^1$ and $R^2$ in formula (1) include arylalkoxy groups in which the alkoxy moiety is a straight- or branched-chain alkoxy group having 1 to 4 carbon atoms, such as benzyloxy, 1-phenylethoxy, 2-phenylethoxy, naphthylmethoxy, anthracenylmethoxy, phenanthrenyl methoxy, etc., with benzyloxy being preferable.

Examples of $C_{2-5}$ alkenyloxy groups represented by $R^1$ and $R^2$ in formula (1) include straight- or branched-chain alkenyloxy groups having 1 to 5 carbon atoms and 1 to 3 (preferably 1) double bonds, such as allyloxy, 2-butenyloxy, 3-methyl-2-butenyloxy, 3-butenyloxy, 4-pentenyloxy, 3-pentenyloxy, etc., with allyloxy and 3-methyl-2-butenyloxy being preferable.

Examples of aryl $C_{2-5}$ alkenyloxy groups represented by $R^1$ and $R^2$ in formula (1) include arylalkenyloxy groups in which the alkenyl moiety is a straight- or branched-chain alkenyl group having 1 to 5 carbon atoms and 1 to 3 (preferably 1) double bonds, such as 3-phenyl-2-propenyloxy, 4-phenyl-2-butenyloxy, 4-phenyl-3-butenyloxy, 5-phenyl-4-pentenyloxy, 5-phenyl-3-pentenyloxy, 4-phenyl-1,3-butadienyloxy, 3-(1-naphthyl)-2-propenyloxy, 3-(2-naphthyl)-2-propenyloxy, etc., with 3-phenyl-2-propenyloxy being preferable.

Examples of $C_{1-5}$ alkylcarbonyl groups represented by $R^4$ in formula (1) include alkylcarbonyl groups in which the alkyl moiety is a straight- or branched-chain alkyl group having 1 to 4 carbon atoms, such as acetyl, propionyl, butyryl, isobutyryl, valeryl, isovaleryl, pivaloyl, 3-methyl-2-butenoyl, etc., with acetyl and 3-methyl-2-butenoyl being preferable.

Examples of aryl $C_{1-4}$ alkyl groups represented by $R^4$ in formula (1) include arylalkyl groups in which the alkyl moiety is a straight- or branched-chain alkyl group having 1 to 4 carbon atoms, such as benzyl, 1-phenethyl, 2-phenethyl, naphthyl methyl, anthracenylmethyl, phenanthrenylmethyl, etc., with benzyl being preferable. The aryl group-forming part of aryl $C_{1-4}$ alkyl groups may have 1 to 5 (preferably 1 to 3) substituents, and examples of the substituents on the aryl group include $C_{1-4}$ alkyl, $C_{1-4}$ alkoxy, $C_{1-4}$ alkylcarbonyl, $C_{1-4}$ alkoxycarbonyl, amino, nitro, cyano, carboxyl, carbamoyl, halogen atom, etc. $C_{1-4}$ alkyl, $C_{1-4}$ alkoxy, and $C_{1-4}$ alkylcarbonyl described herein are the same as $C_{1-4}$ alkyl, $C_{1-4}$ alkoxy, and $C_{1-4}$ alkylcarbonyl described above. Examples of $C_{1-4}$ alkoxycarbonyl groups include alkoxycarbonyl groups in which the alkoxy moiety is a straight- or branched-chain alkoxy group having 1 to 4 carbon atoms, such as methoxycarbonyl, ethoxycarbonyl, isopropoxycarbonyl, tert-butoxycarbonyl, etc. Examples of the halogen atom include fluorine, chlorine, bromine, iodine, etc.

The bis(tetrahydrofuran) compounds represented by formula (1) include the compounds represented by the following formulae (1A), (1B), (1C), and (1D):

[Chem. 3]

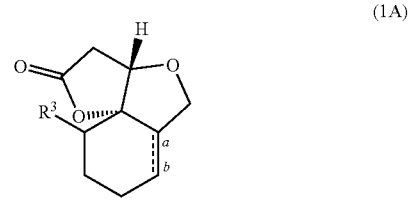

(1A)

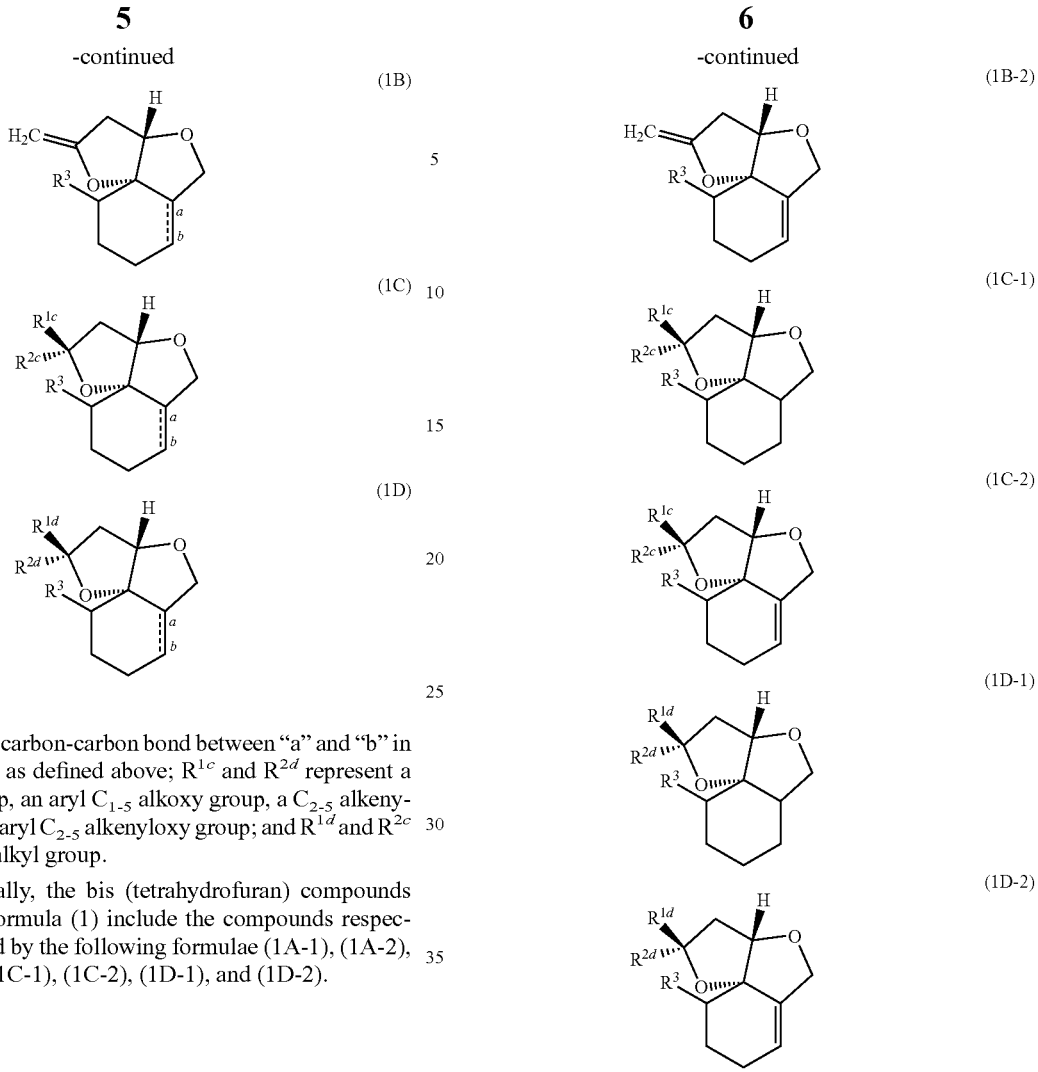

wherein $R^3$ and a carbon-carbon bond between "a" and "b" in each formula are as defined above; $R^{1c}$ and $R^{2d}$ represent a $C_{1-5}$ alkoxy group, an aryl $C_{1-5}$ alkoxy group, a $C_{2-5}$ alkenyloxy group, or an aryl $C_{2-5}$ alkenyloxy group; and $R^{1d}$ and $R^{2c}$ represent a $C_{1-4}$ alkyl group.

More specifically, the bis (tetrahydrofuran) compounds represented by formula (1) include the compounds respectively represented by the following formulae (1A-1), (1A-2), (1B-1), (1B-2), (1C-1), (1C-2), (1D-1), and (1D-2).

[Chem. 4]

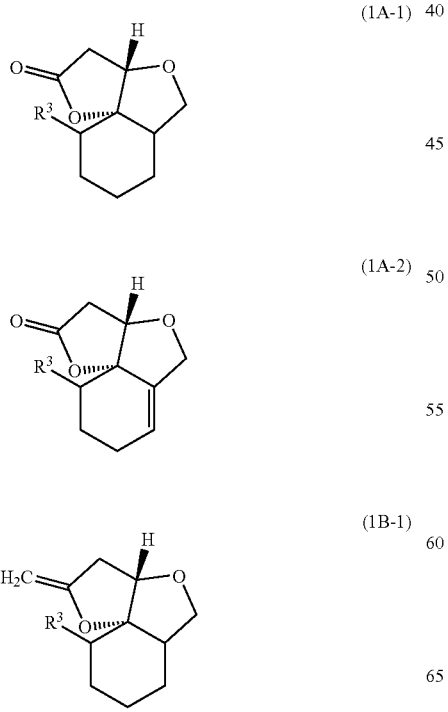

wherein $R^{1c}$, $R^{1d}$, $R^{2c}$, $R^{2d}$, and $R^3$ in each formula are as defined above.

$R^3$ in the compounds represented by the above formulae (1A-1), (1A-2), (1B-1), (1B-2), (1C-1), (1C-2), (1D-1), and (1D-2) is preferably a hydrogen atom.

The bis(tetrahydrofuran) compounds represented by formula (1) of the present invention are produced, for example, according to the processes expressed by the following reaction formula-1 to reaction formula-3.

Reaction Formula-1

[Chem. 5]

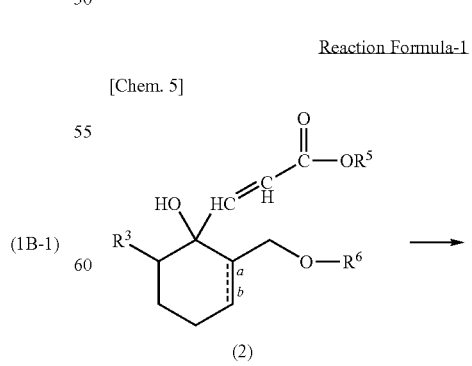

wherein $R^3$ and a carbon-carbon bond between "a" and "b" in each formula are as defined above; $R^5$ represents a $C_{1-4}$ alkyl group; and $R^6$ represents a silyl-based protecting group.

As shown in reaction formula-1, the bis(tetrahydrofuran) compound (1A) of the present invention is produced by reacting a compound represented by formula (2) with a quaternary ammonium fluoride.

In the above formula (2), $R^5$ is a straight- or branched-chain $C_{1-4}$ alkyl group having 1 to 4 carbon atoms.

Examples of silyl-based protecting group represented by $R^6$ include silyl groups such as trimethylsilyl (TMS), triethylsilyl (TES), triisopropylsilyl (TIPS), triisobutylsilyl, tert-butyldimethylsilyl (TBS), tert-butylmethoxyphenylsilyl (TBMPS), tert-butyldiphenylsilyl (TBDPS), tert-hexyldimethylsilyl (TDS), triphenylsilyl (TPS), etc., with tert-butyldimethylsilyl and tert-butyldiphenylsilyl being preferable.

This reaction is preferably carried out in a solvent. A wide variety of well-known solvents may be used insofar as they do not adversely affect the reaction. Examples of such solvents include aromatic hydrocarbons such as benzene, toluene, xylene, etc.; halogenated aromatic hydrocarbons such as chlorobenzene, dichlorobenzene, etc.; aliphatic hydrocarbons such as hexane, cyclohexane, petroleum ether, etc.; aliphatic hydrocarbon halides such as dichloromethane, 1,2-chloroethane, chloroform and carbon tetrachloride; ethers such as diethyl ether, diisopropyl ether, dioxane, tetrahydrofuran, ethylene glycol dimethyl ether, ethylene glycol diethyl ether, etc.; ketones such as acetone, 2-butanone, methyl isobutyl ketone, etc.; nitriles such as acetonitrile, propionitrile, benzonitrile, etc.; amides such as N,N-dimethylformamide, hexamethylphosphoric triamide (HMPA), etc.; sulfoxides such as dimethyl sulfoxide, etc.; or a mixed solvent of the above solvents.

Examples of quaternary ammonium fluorides used in this reaction include tetrabutylammonium fluoride (TBAF), tetraethylammonium fluoride (TEF), ammonium fluoride, etc., with tetrabutylammonium fluoride being preferable.

The amount of quaternary ammonium fluoride used is not particularly limited, and is suitably selected from a wide range. The amount of quaternary ammonium fluoride used is usually 0.5 to 5 moles, preferably 1.5 to 3 moles, per mole of compound (2).

The reaction temperature is not particularly limited; however, suitable reaction temperatures are usually within a range of −10° C. to the boiling point of the solvent used, preferably about 0 to about 50° C., and further preferably about 10 to about 40° C. Additionally, the reaction time is usually within 10 hours, preferably from about 30 minutes to about 5 hours, although the reaction time depends on conditions such as the type of raw material compounds, the amount of raw material compounds used, the reaction temperature, etc.

Bis(tetrahydrofuran) compound (1A) thus obtained is easily isolated and purified from the reaction mixture by typical isolation and purification procedures, such as column chromatography and recrystallization.

Compound (1B) is produced in accordance with the process expressed by the following reaction formula-2:

Reaction Formula-2

[Chem. 6]

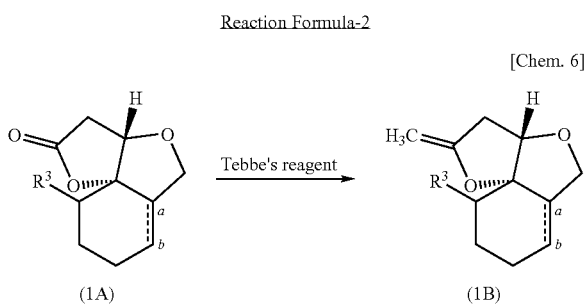

(1A)     (1B)

wherein $R^3$ and a carbon-carbon bond between "a" and "b" are as defined above.

As shown in reaction formula-2, compound (1B) is produced by reacting compound (1A), produced according to the reaction formula-1, with Tebbe's reagent.

With regard to Tebbe's reagent, reaction conditions, and the like, refer to J. Am. Chem. Soc., 100, 3611 (1978), J. Am. Chem. Soc., 119, 7483 (1997), etc. The process expressed by reaction formula-2 is carried out by, for example, adding Tebbe's reagent dropwise to compound (1A) at room temperature in a solvent such as THF, toluene, or pyridine, preferably in an anhydrous solvent, stirring the mixture for one to several hours at room temperature, adding dropwise thereto an aqueous alkali solution such as a 10% aqueous sodium hydroxide solution while cooling, and filtering and concentrating the resulting reaction solution.

Compound (1B) thus obtained is easily isolated from a reaction mixture by typical isolation and purification procedures, such as column chromatography and recrystallization.

Reaction Formula-3

[Chem. 7]

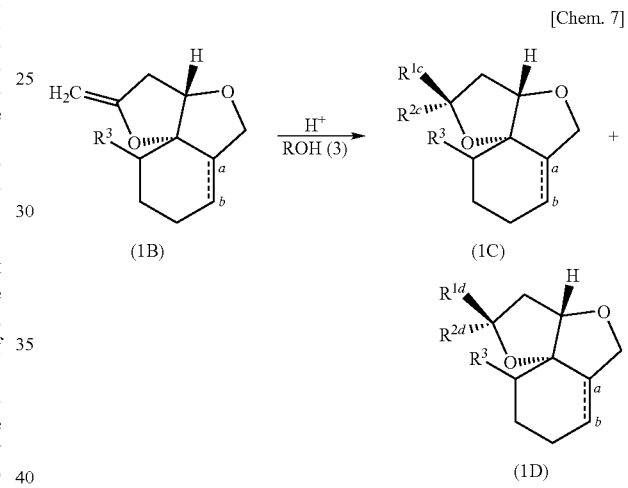

wherein $R^{1c}$, $R^{1d}$, $R^{2c}$, $R^{2d}$, $R^3$ and a carbon-carbon bond between "a" and "b" are as defined above; and R is the same as $R^{1c}$ or $R^{2d}$, and represents a $C_{1-5}$ alkoxy group, an aryl $C_{1-5}$ alkoxy group, a $C_{2-5}$ alkenyloxy group, or an aryl $C_{2-5}$ alkenyloxy group.

As shown in reaction formula-3, bis(tetrahydrofuran) compounds (1C) and (1D) are produced by reacting compound (1B) in an alcohol represented by formula (3), in the presence of an acid catalyst.

Specific examples of alcohol (3) used in this reaction include, for example, methanol, ethanol, n-propyl alcohol, isopropyl alcohol, n-butyl alcohol, isobutyl alcohol, sec-butyl alcohol, tert-butyl alcohol, prenyl alcohol(3-methyl-2-butenonol), benzyl alcohol, allyl alcohol, cinnamyl alcohol, etc., with methanol, ethanol, n-propyl alcohol, and isopropyl alcohol being preferable, and methanol, ethanol, and n-propyl alcohol being particularly preferable.

The amount of alcohol (3) used is not particularly limited, and is suitably selected from a wide range. Alcohol (3) is usually used in an amount of 0.8 moles or more, preferably 1.2 moles or more, per mole of compound (1B). As alcohol (3) is usually used as a solvent, alcohol (3) is used in an amount of 1 to 1,000 parts by weight, preferably 10 to 100 parts by weight, per part by weight of compound (1B).

This reaction may be carried out by further adding a suitable solvent. A wide variety of well-known solvents may be used insofar as they do not adversely affect the reaction. THF, dichloromethane, etc. are examples of usable solvents.

Examples of catalysts used in this reaction include: pyridinium p-toluenesulfonate (PPTS), pyridinium dodecylbenzenesulfonate, pyridinium tetrafluoroborate, pyridinium hydrogen sulfate, pyridine-$SO_3$ complex, p-toluenesulfonate, benzenesulfonic acid, dodecylbenzenesulfonic acid, p-toluenesulfonic acid chloride, p-toluenesulfonic acid anhydride, benzoyl chloride, 2,4,6-trimethylbenzoyl chloride, sulfuric acid, amidosulfuric acid (sulfamic acid), sodium hydrogen sulfite, anhydrous zinc chloride, anhydrous ferric chloride (III), anhydrous aluminum chloride, Scandium(III) trifluoromethanesulfonate, yttrium(III) trifluoromethanesulfonate, ytterbium(III) trifluoromethanesulfonate, iodine, etc. Among these, pyridinium salt compounds such as pyridinium p-toluenesulfonate, pyridinium dodecylbenzenesulfonate, pyridinium tetrafluoroborate, and pyridinium hydrogen sulfate are preferable, and pyridinium p-toluenesulfonate is particularly preferable.

The amount of catalyst used is usually about 0.1 to about 30 wt %, preferably about 5 to about 20 wt %, based on compound (1B).

The reaction temperature is not particularly limited; however, suitable reaction temperatures are usually within a range of −10° C. to the boiling point of the solvent used, preferably 0 to 50° C., and further preferably in the vicinity of 0° C. Additionally, the reaction time is usually from about 1 to about 60 minutes, preferably about 5 minutes, although the reaction time depends on reaction conditions such as the type of raw material compounds, the amount of raw material compounds used, the reaction temperature, etc.

Compounds (1C) and (1D) thus obtained are easily isolated from a reaction mixture by typical isolation and purification procedures such as column chromatography and recrystallization.

This reaction produces a mixture of compounds (1C) and (1D). However, these compounds are easily isolated and purified by isolation procedures such as silica gel column chromatography and the like. As a result, in this reaction, compound (3) is produced in an amount about 2 to about 4 times the amount of compound (4).

Raw material compound (2) used in reaction formula-1 is producible in accordance with a known method.

For example, raw material Compound (2) can be produced in accordance with the process expressed by the following reaction formula-4.

Reaction Formula-4

[Chem. 8]

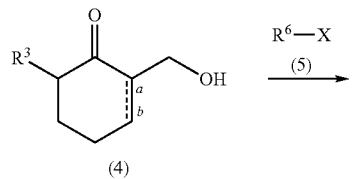

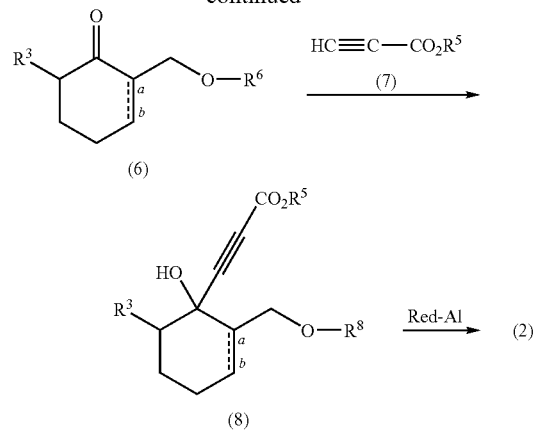

wherein $R^3$, $R^5$ and $R^6$ and a carbon-carbon bond between "a" and "b" are as defined above; and X represents a halogen atom.

As shown in reaction formula-4, compound (2) is produced by reacting compound (4) with a silyl halide compound represented by formula (5), thereby protecting a hydroxy group of compound (4) with a silyl-based protecting group, then reacting thus-obtained compound (6) with a propynoic acid ester represented by formula (7) in the presence of a strong base such as lithium diisopropylamide (LDA), and further reducing thus-obtained compound (8) using sodium bis(2-methoxyethoxy)aluminum hydride (Red-Al).

These reactions are carried out by employing known reaction conditions, or in accordance with known methods.

As is clear from the test example described later, bis(tetrahydrofuran) compound (1) of the present invention is capable of enhancing neurotrophic factor activity. Accordingly, the bis(tetrahydrofuran) compound represented by formula (1) of the present invention, particularly the compounds represented by formulae (1C) and (1D), are effective as neurotrophic factor activity enhancers, and are also effective as active ingredients of a composition used for ameliorating or treating diseases and other conditions caused by neurological disorders.

Neurotrophic factors contemplated by the present invention include nerve growth factor (NGF), brain-derived neurotrophic factor (BDNF), neurotrophin-3 (NT-3), glial-derived neurotrophic factor (GDNF), NT-4/5, etc., with NGF or BDNF being preferable, and NGF being particularly preferable.

The present invention provides a neurotrophic factor activity enhancer or a composition for ameliorating diseases and other conditions caused by neurological disorders (hereinafter also referred to as a "preparation"), wherein the enhancer and the composition contains the bis(tetrahydrofuran) compound represented by formula (1) as an active ingredient.

The preparation of the present invention may consist of compound (1) alone, or the preparation of the present invention may be a composition prepared by combining compound (1) with any known carriers, additives, or the like into a form suitable for a desired use according to a known method.

The form of the preparation of the present invention is not particularly limited. Examples of the form include solid preparations such as tablets, powders, granules, pills, powdered syrups, and capsules (hard capsules and soft capsules); paste-like or gel-like preparations such as creams, ointments, and gels; and liquid preparations such as solutions, suspensions, emulsions, syrups, and elixirs.

The content of bis(tetrahydrofuran) compound (1) in the preparation of the present invention is not particularly limited insofar as the neurotrophic factor activity-enhancing effect is exhibited. Of the total weight (100 wt %) of the preparation, the content of bis(tetrahydrofuran) compound (1) is usually in the range of 0.001 to 99 wt %, preferably 0.01 to 50 wt %, more preferably 0.1 to 30 wt %.

The preparation of the present invention contains bis(tetrahydrofuran) compound (1) in an amount effective for exhibiting a neurotrophic factor activity-enhancing effect. The preparation may be combined with one or more other components within a range in which the above-described effect is not impaired. Such other components are not limited insofar as they are pharmacologically and pharmaceutically acceptable. Such components include carriers generally used for production of preparations, for example, diluents, binders, dispersants, thickeners, lubricants, pH adjusters, solubilizers, etc. Other components include antibiotics, antimicrobial agents, bactericides, antiseptics, builders, bleaches, enzymes, chelating agents, antifoaming agents, colorants (such as dye compounds and pigments), softeners, humectants, surfactants, antioxidants, perfumes, flavoring agents, odor improving agents, solvents, etc. Further, known neurotrophic factors, neurotrophic factor-like active substances, or neurotrophic factor activity enhancers or activators other than the enhancers of the present invention may be added to the preparation of the present invention.

Methods of the use of the present preparation include a method in which the preparation is introduced into the body via oral administration, instillation, injection, etc., and a method in which the preparation is locally applied to the affected area.

Because the amount used of the preparation of the present invention depends on the formulation, administration (use), and the like, the amount is not necessarily determined; however, an appropriate daily dose can be suitably set according to the age and symptoms of the patient, and is usually within a range of 1 ng to 100 mg, preferably 10 ng to 50 mg, per 1 kg of human adult body weight, in terms of dosage of bis(tetrahydrofuran) compound (1) of the present invention. The preparations are preferably administrated in one to several divided doses per day.

EXAMPLE

The present invention is described below in further detail with reference to production examples, a preparation example, and a test example of bis(tetrahydrofuran) compound (1) of the present invention; however, the present invention is not limited thereto. "Me" used hereinbelow refers to methyl.

Measuring Device Used

The nuclear magnetic resonance spectrum (hereinbelow referred to as "NMR") was measured using Varian Gemini-200, Mercury-300, Unity-600 and JOEL JMN-ECP-400. A sample was measured using tetramethyl silane (TMS), chloroform ($CHCl_3$) or benzene ($C_6H_6$) as the internal standard. The chemical shift ($\delta$) was indicated in ppm, and the coupling constant (J) was indicated in Hz. The signals were described with the following symbols: "s" for singlet, "d" for doublet, "t" for triplet, "q" for quartet, "m" for multiplet, and "br" for broad.

Normal-phase silica gel column chromatography was performed using Merck Kieselgel 60 (70-230 mesh ASTM) and Kanto Chemical normal-phase silica gel 60 (spherical, 63-210 μm), and reversed-phase column chromatography was performed using a Nacalai Tesque Cosmosil 140 $C_{18}$-PREP.

High-performance liquid chromatography (HPLC) was performed using a JASCO 880-PU chromatographic pump, and the results were expressed in v/w ratio using a JASCO spectrometer. The melting point (hereinafter sometimes referred to as "mp") was measured using a YANACO micro melting point apparatus.

The infrared absorption spectrum (hereinafter may be referred to as "IR") was measured by the reflection method using a FT-IR410.

The mass analysis spectrum (hereinafter may be referred to as "MS") was measured by the electron impact ionization method (hereinafter may be referred to as "EI"), the chemical ionization method (hereinafter may be referred to as "CI"), or the fast atom bombardment method (hereinafter may be referred to as "FAB"), using a JEOL AX-500.

X-ray crystallographic analysis (X-ray) was carried out using a Mac Science DIP-2020 X-ray analyzer. Mo Ka radiation was used as the X-ray source. Reflection data were collected, and analysis was carried out using a MAC Science crystal analysis program.

Solvent and Reagent Used Unless otherwise specifically stated, the reactions were carried out under Ar (argon) atmosphere, and special grade solvents or dehydrated solvents were used as reaction solvents. Further, the anhydrous tetrahydrofuran (THF) used was anhydrous tetrahydrofuran (stabilizer-free) produced by Kanto Chemical Co., Inc.; the anhydrous dichloromethane used was anhydrous dichloromethane produced by Kanto Chemical Co., Inc.

The product obtained upon solvent extraction was and dried using anhydrous magnesium sulfate ($MgSO_4$) or anhydrous sodium sulfate ($Na_2SO_4$). The solvent was evaporated with an evaporator under reduced pressure.

Thin layer chromatography (TLC) for analysis was performed using Merck Kieselgel 60F 254 (0.25 mm, 0.5 mm). Spots were detected by irradiation using a 254 nm UV lamp, or by spraying with an anisaldehyde-sulfuric acid color-developing agent, and then heating.

Production Example 1

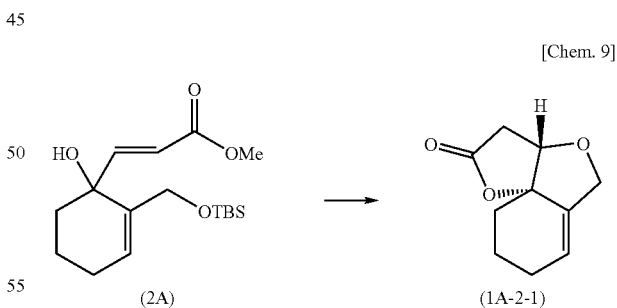

[Chem. 9]

TBAF (1.0 M, THF, 13,78 ml, 13.78 mmol) was added dropwise to an anhydrous THF solution (45 ml) of the above-described ester compound (2A) (1.5 g, 4.59 mmol) that corresponds to raw material compound (2) of the present invention, and the mixture was stirred for 30 minutes at room temperature. Saturated saline was added thereto, and the mixture was thrice-extracted with ethyl acetate. The organic layer thus obtained was dried with anhydrous sodium sulfate, filtered, and then concentrated. The residue was purified by column chromatography (silica gel 30 g, n-hexane:ethyl acetate=1:1) to afford bis(tetrahydrofuran) compound (1A-2-1) of the present invention (757.5 mg, yield 92%).

FTIR (neat) 3526, 2945, 2319, 1790 cm$^{-1}$ $^1$H NMR (300 MHz, CDCl$_3$) δ ppm: 1.49-1.59 (1H, m), 1.83-1.92 (2H, m), 1.96-2.32 (3H, m), 2.79 (2H, d, J=3.6 Hz), 4.31 (1H, dd, J=1.8, 3.6 Hz), 4.39 (1H, dd, J=2.1, 12.0 Hz), 4.57 (1H, dq, J=2.1, 12.0 Hz), 5.93 (1H, m)

$^{13}$C NMR (75 MHz, CDCl$_3$) δ ppm: 17.2t, 24.1t, 29.1t, 36.9t, 69.8t, 81.9d, 88.1s, 125.4d, 134.6s, 174.83s MS (CI) m/z 181 (M$^+$+H)

HRMS (CI) m/z calcd for C$_{10}$H$_{13}$O$_3$ (M$^+$+H): 181.0865, found 181.0862 m.p. 68-71° C.

Production Example 2

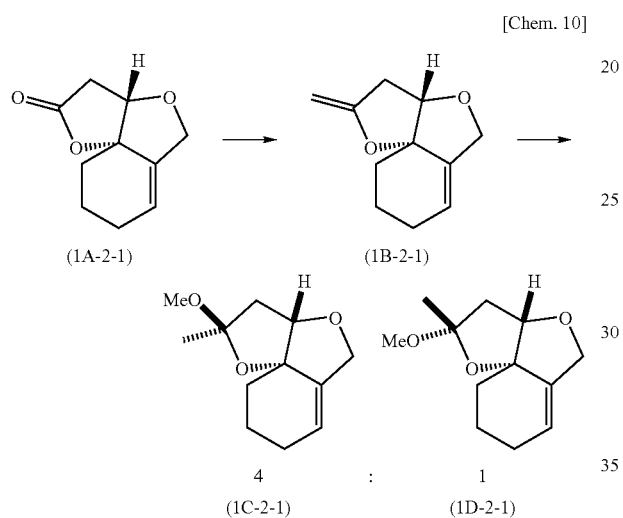

[Chem. 10]

(1A-2-1)   (1B-2-1)

4 : 1

(1C-2-1)   (1D-2-1)

Anhydrous THF (6 ml), anhydrous toluene (2 ml), anhydrous pyridine (40 μl, 0.49 mmol) and bis(tetrahydrofuran) compound (1A-2-1) (400 mg, 2.197 mmol) of the present invention obtained in Production Example 1 were placed in a dried two-neck flask. Tebbe's reagent (0.5 M, toluene, 8.79 ml, 4.39 mmol) was further added dropwise thereto at room temperature. This mixture was stirred for one hour at room temperature, and then cooled to −20° C. A 10% aqueous sodium hydroxide solution was added dropwise thereto, and the mixture was then filtered through Celite and concentrated. The residue thus obtained was used in the next process without purification.

The thus-obtained residue was dissolved in methanol (30 ml), and PPTS (301.46 mg, 1.2 mmol) was added thereto at room temperature, and the mixture was stirred for 5 hours. The mixture was cooled to 0° C., and then saturated sodium hydrogen carbonate solution was added thereto, after which the mixture was thrice-extracted with ethyl acetate. The organic layer thus obtained was dried with anhydrous sodium sulfate, filtered, and then concentrated. The residue was purified by column chromatography (silica gel 1.5 g, the ratio of n-hexane to ethyl acetate=3:1) to give a colorless oily diastereomer mixture of (1C-2-1) and (1D-2-1) (369 mg, yield 80%). Next, the thus-obtained diastereomer mixture was separated into compound (1C-2-1) and compound (1D-2-1) by normal-phase HPLC (Cosmosil 5SL-II Water (20×250), the ratio of n-hexane to ethyl acetate=6:1, 17.0 ml/min, detector: RI).

Physical Properties of Compound (1C-2-1):

FTIR (neat) 2985, 2943, 2863, 2830, 1698 cm$^{-1}$ $^1$H NMR (300 MHz, C$_6$D$_6$) δ ppm: 1.13 (1H, dt, J=3.0, 12.9 Hz), 1.43 (3H, s), 1.52-1.60 (1H, m), 1.64-1.79 (1H, m), 1.85-2.00 (2H, m), 2.14 (1H, dt, J=3.3, 9.7 Hz), 2.26 (1H, dd, J=1.7, 14.3 Hz), 2.24 (1H, dd, J=5.8, 14.3 Hz), 3.15 (3H, s), 4.16 (1H, dq, J=1.7, 11.5 Hz), 4.23 (1H, dd, J=1.7, 5.8 Hz), 4.55 (1H, dq, J=3.0, 11.5 Hz), 5.31 (1H, brs)

$^{13}$C NMR (150 MHz, C$_6$D$_6$) δ ppm: 18.7t, 23.4q, 24.7t, 30.2t, 47.7t, 48.7q, 69.8t, 87.6s, 88.2d, 109.9s, 121.04d, 139.8s MS (CI) m/z 209 (M$^+$−H)

HRMS (CI) m/z calcd for C$_{12}$H$_{17}$O$_3$ (M$^+$−H): 209.1205, found 209.1155.

Physical Properties of Compound (1D-2-1):

FTIR (neat) 2984, 2939, 2870, 2829, 1431, 1375 cm$^{-1}$ $^1$H NMR (300 MHz, C$_6$D$_6$) δ ppm: 1.16 (1H, ddd, J=3.3, 12.6, 13.8 Hz), 1.30 (3H, s), 1.46-1.55 (1H, m), 1.67-1.83 (3H, m), 1.87-2.09 (2H, m), 2.52 (1H, d, J=14.1 Hz), 3.20 (3H, s), 4.26 (1H, d, J=6.0 Hz), 4.24 (1H, dd, J=1.4, 10.7 Hz), 4.83 (1H, dq, J=2.1, 10.7 Hz), 5.36 (1H, brs)

$^{13}$C NMR (150 MHz, C$_6$D$_6$) δ ppm: 18.5t, 23.6q, 24.5t, 32.2t, 47.3t, 48.7q, 70.7t, 87.6s, 87.9d, 108.3s, 121.0d, 140.3s MS (CI) m/z 209 (M$^+$−H)

HRMS (CI) m/z calcd for C$_{12}$H$_{17}$O$_3$(M$^+$−H): 209.1178, found 209.1177.

Production Example 3

[Chem. 11]

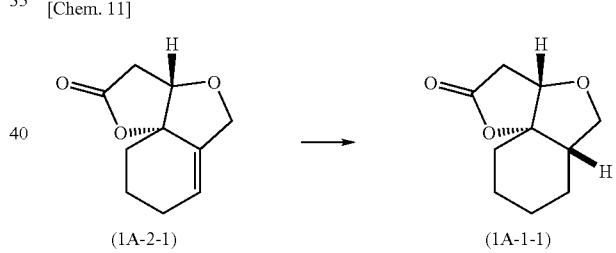

(1A-2-1)   (1A-1-1)

The tetrahydrofuran compound (1A-2-1) (1 g, 5.5 mmol) of the present invention obtained in Production Example 1 above was dissolved in methanol (55 ml), and palladium-activated carbon (290 mg as activated carbon palladium) was added thereto, and the mixture was stirred for 12 hours at room temperature under 1 atm of hydrogen. The reaction mixture thus obtained was filtered and then concentrated. The residue was purified by column chromatography (silica gel 20 g, the ratio of n-hexane to ethyl acetate=3:1) to afford, as a colorless oily product, the tetrahydrofuran of the present invention compound (1A-1-1) (838 mg, yield 83%).

FTIR (neat) 2938, 2862, 1773, 1451 cm$^{-1}$ $^1$H NMR (600 MHz, CDCl$_3$) δ ppm: 1.26-1.38 (3H, m), 1.64-1.77 (1H, m), 1.84-1.94 (4H, m), 2.31 (1H, quintet, J=4.9 Hz), 2.67 (1H, d, J=18.4 Hz), 2.76 (1H, dd, J=5.5, 18.4 Hz), 3.65 (1H, d, J=8.5 Hz), 4.07 (1H, dd, J=4.4, 8.5 Hz), 4.55 (1H, d, J=5.5 Hz)

$^{13}$C NMR (75 MHz, CDCl$_3$) δ ppm: 23.1t, 23.8t, 28.3t, 30.0t, 36.4t, 44.0d, 73.7t, 78.0d, 95.4s, 175.4s MS (CI) m/z 183 (M$^+$+H)

HRMS (CI) m/z calcd for $C_{10}H_{15}O_3(M^++H)$: 183.1021, found 183.1024.

Production Example 4

[Chem. 12]

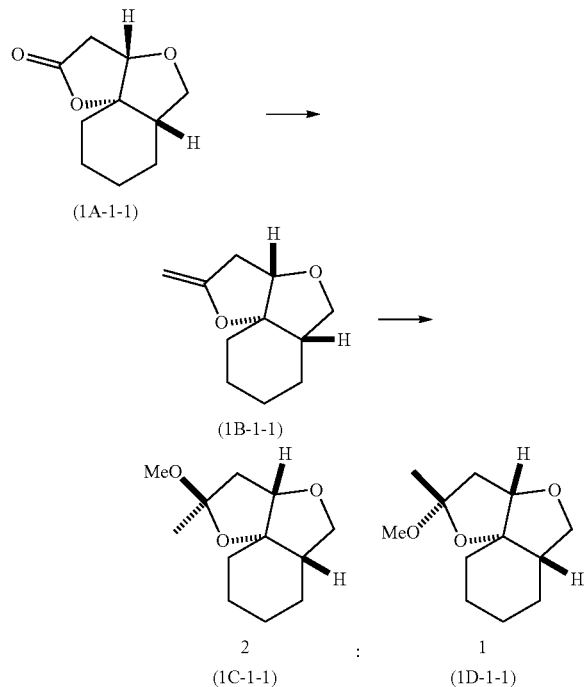

Anhydrous THF (5 ml), anhydrous toluene (1.6 ml), anhydrous pyridine (30 ml, 0.37 mmol) and bis(tetrahydrofuran) compound (1A-1-1) (300 mg, 1.66 mmol) of the present invention obtained in Production Example 3 above were placed in a dried two-neck flask. Tebbe's reagent (0.5 M, toluene, 6.6 ml, 3.29 mmol) was further added dropwise thereto at room temperature. This mixture was stirred for 2 hours at room temperature, and then cooled to −20° C. A 10% aqueous sodium hydroxide solution was added dropwise thereto, and the mixture was then filtered through Celite and concentrated. The residue thus obtained was used in the next process without purification.

The thus-obtained residue was dissolved in methanol (16 ml), PPTS (164.8 mg, 0.66 mmol) was added thereto at room temperature, and the mixture was stirred for 5 hours. The mixture was cooled to 0° C., and then saturated sodium hydrogen carbonate solution was added thereto, after which the mixture was thrice-extracted with ethyl acetate. The organic layer thus obtained was dried with anhydrous sodium sulfate, filtered, and then concentrated. The residue was purified by column chromatography (silica gel 10 g, the ratio of n-hexane to ethyl acetate=2:1) to give a colorless oily diastereomer mixture of (1D-1-1) and (1C-1-1) (278 mg, yield 80%). Next, the thus-obtained diastereomer mixture was separated into (1D-1-1) and (C-1-1) by normal-phase HPLC (Cosmosil 5SL-II Water (20×250), the ratio of n-hexane to ethyl acetate=6:1, 17.0 ml/min, detector: RI).

Physical Properties of Compound (1C-1-1):
FTIR (neat) 2984, 2934, 2860, 2826, 1451, 1375 cm$^{-1}$
$^1$H NMR (300 MHz, $C_6D_6$) δ ppm: 0.99 (2H, dt, J=3.0, 11.0 Hz), 1.06-1.24 (1H, m), 1.40 (3H, s), 1.45-1.67 (4H, m), 1.91 (1H, dt, J=5.0, 11.5 Hz), 2.12 (1H, brd, J=11.5 Hz), 2.21 (1H, d, J=14.4 Hz), 2.28 (1H, dd, J=6.3, 14.4 Hz), 3.17 (3H, s), 3.43 (1H, d, J=7.7 Hz), 4.05 (1H, dd, J=4.5, 7.7 Hz), 4.40 (1H, dd, J=1.1, 6.3 Hz)
$^{13}$C NMR (75 MHz, $C_6D_6$) δ ppm: 22.8q, 24.3t, 24.7t, 29.3t, 32.1t, 45.8d, 48.3t, 48.7q, 73.4t, 83.2d, 94.3s, 108.9s
MS (CI) m/z 213 (M$^+$+H)
HRMS (CI) m/z calcd for $C_{12}H_{20}O_3(M^++H)$:213.1491, found 213.1471.

Physical Properties of Compound (1D-1-1):
FTIR (neat) 2982, 2934, 2856, 2826, 1449, 1375 cm$^{-1}$
$^1$H NMR (300 MHz, $C_6D_6$) δ ppm: 0.88-1.09 (2H, m), 1.21 (1H, dq, J=3.4, 13.2 Hz), 1.31 (3H, s), 1.31-1.62 (5H, m), 1.68 (1H, dd, J=5.3, 14.1 Hz), 1.88 (1H, dt, J=5.3, 11.4 Hz), 2.48 (1H, d, J=14.1 Hz), 3.22 (3H, s), 3.47 (1H, d, J=7.5 Hz), 4.22 (1H, d, J=5.4 Hz), 4.37 (1H, dd, J=4.3 Hz)
$^{13}$C NMR (75 MHz, $C_6D_6$) δ ppm: 24.3q, 24.6t, 24.7t, 29.8t, 33.0t, 46.0d, 46.4t, 49.0q, 74.0t, 83.2d, 95.2s, 108.1s
MS (CI) m/z 211 (M$^+$+H)
HRMS (CI) m/z calcd for $C_{12}H_{19}O_3(M^+-H)$: 211.1334, found 211.1353.

Production Example 5

Anhydrous THF (5 ml), anhydrous toluene (1.6 ml), anhydrous pyridine (30 ml, 0.37 mmol) and bis(tetrahydrofuran) compound (1A-1-1) (300 mg, 1.66 mmol) of the present invention obtained in Production Example 3 above were placed in a dried two-neck flask. Tebbe's reagent (0.5 M, toluene, 6.6 ml, 3.29 mmo) was further added dropwise thereto at room temperature. This mixture was stirred for 2 hours at room temperature, and then cooled to −20° C. A 10% aqueous sodium hydroxide solution was added dropwise thereto, and the mixture was then filtered through Celite and concentrated. The residue thus obtained was used in the next process without purification.

The thus-obtained residue was dissolved in benzyl alcohol (16 ml), and PPTS (164.8 mg, 0.66 mmol) was added thereto at room temperature, and the mixture was stirred for 5 hours. The mixture was cooled to 0° C., and then saturated sodium hydrogen carbonate solution was added thereto, after which the mixture was thrice-extracted with ethyl acetate. The organic layer thus obtained was dried with anhydrous sodium sulfate, filtered, and then concentrated. The residue was purified by column chromatography (silica gel 10 g, the ratio of n-hexane to ethyl acetate=2:1) to give a colorless oily diastereomer mixture of (1C-2-2) and (1D-2-2) (278 mg, yield 80%). Next, the thus-obtained diastereomer mixture was separated into the (1C-2-2) and (1D-2-2) shown below by normal-phase HPLC (Cosmosil 5SL-II Water (20×250), the ratio of n-hexane to ethyl acetate=6:1, 17.0 ml/min, detector: RI).

[Chem. 13]

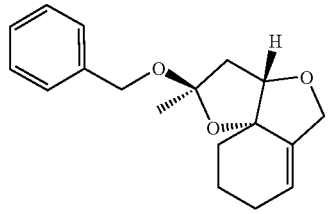

(1C-2-2)

-continued (1D-2-2)

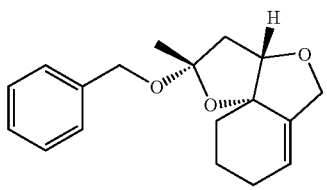

Physical Properties of Compound (1C-2-2):

$^1$H NMR (600 MHz in $C_6D_6$) δ ppm: 1.07 (1H, dt, 3.9, 14.4 Hz), 1.50 (1H, m), 1.52 (3H, s), 1.70 (1H, m), 1.89 (2H, m), 2.16 (1H, dt, J=3.0, 14.4 Hz), 2.35 (1H, dd, J=2.4, 15.0 Hz), 2.51 (1H, dd, J=6.0, 15.0 Hz), 4.17 (1H, dd, J=2.4, 12.0 Hz), 4.20 (1H, dd, J=2.4, 7.2 Hz), 4.48 (1H, d, J=12.0 Hz), 4.55 (1H, dq, J=, 3.0, 12.0 Hz), 4.68 (1H, d, J=12.0 Hz), 5.31 (1H, br s), 7.11 (1H, t, J=8.4 Hz), 7.20 (2H, t, J=8.4 Hz), 7.34 (2H, d, J=8.4 Hz)

$^{13}$C NMR (150 MHz in $C_6D_6$) δ ppm: 18.60t, 24.48q, 24.68t, 30.05t, 47.98t, 63.96t, 69.92t, 87.97s, 88.14d, 110.12s, 121.17d, 127.32d, 127.72d (2C), 128.48d (2C), 139.73s, 139.88s.

Physical Properties of Compound (1D-2-2):

$^1$H NMR (600 MHz in $C_6D_6$) δ ppm: 1.16 (1H, ddd, J=3.3, 12.6, 14.6 Hz), 1.37 (3H, s), 1.53 (1H, m), 1.73 (2H, dt, J=3.3, 11.4 Hz), 1.76 (2H, dd, J=5.6, 14.3 Hz), 1.77 (1H, m), 1.74 (1H, br d, J=11.4 Hz), 2.24 (1H, m), 2.62 (1H, d, J=14.3 Hz), 4.14 (1H, dd, J=1.6, 11.4 Hz), 4.22 (1H, d, J=5.8 HZ), 4.59 (1H, d, J=12.0 Hz), 4.70 (1H, d, J=12.0 Hz), 4.79 (1H, ddt, J=2.2, 3.0, 11.4 Hz), 5.31 (1H, br s), 7.08 (1H, t, J=7.4 Hz), 7.18 (2H, t, J=8.4 Hz), 7.38 (2H, d, J=7.4 Hz)

$^{13}$C NMR (150 MHz in $C_6D_6$) δ ppm: 18.48t, 24.57t, 24.75q, 32.16t, 47.48t, 63.82t, 70.74t, 87.90d, 87.95s, 108.77s, 121.16d, 127.14d, 127.84d (2C), 128.00d (2C), 139.98s, 140.21s.

Production Example 6

A colorless oily diastereomer mixture of (1C-2-3) and (1D-2-3) was obtained in a similar manner as in Production Example 5, except that ethyl alcohol (16 ml) was used instead of benzyl alcohol. Next, the diastereomer mixture thus obtained was separated into the (1C-2-3) and (1D-2-3) shown below by normal-phase HPLC (Cosmosil 5SL-II Water (20× 250), the ratio of n-hexane to ethyl acetate=6:1, 17.0 ml/min, detector: RI).

[Chem. 14]

(1C-2-3)

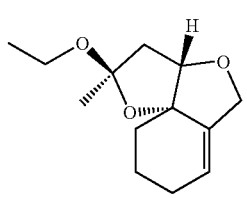

(1D-2-3)

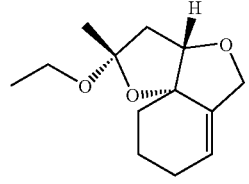

Physical Properties of Compound (1C-2-3):

$^1$H NMR (600 MHz in $C_6D_6$) δ ppm: 1.11 (3H, t, J=6.9 Hz), 1.15 (1H, ddd, J=3.0, 12.9, 13.2 Hz), 1.48 (3H, s), 1.58 (1H, m), 1.74 (1H, m), 1.90 (2H, m), 2.19 (1H, dt, J=3.3, 13.2 Hz), 2.31 (1H, dd, J=1.6, 14.0 Hz), 2.67 (1H, dd, J=5.8, 14.0 Hz), 2.67 (1H, dd, J=5.8, 14.0 Hz), 3.37 (1H, dq, J=6.9, 16.2 Hz), 3.62 (1H, dq, J=3.9, 16.2 Hz), 4.17 (1H, ddt, J=1.6, 1.9, 13.8 Hz), 4.24 (1H, dd, J=1.4, 6.0 Hz), 4.54 (1H, dddd, J=2.1, 3.0, 8.4, 13.8 Hz), 5.31 (1H, br s)

$^{13}$C NMR (150 MHz in $C_6D_6$) δ ppm: 15.89q, 18.58t, 24.24q, 24.69t, 30.31t, 47.99t, 56.72t, 69.87t, 87.53s, 88.22d, 109.70s, 120.96d, 139.89s.

Physical Properties of Compound (1D-2-3):

$^1$H NMR (300 MHz in $C_6D_6$) δ ppm: 1.14 (3H, t, J=6.9 Hz), 1.17 (1H, m), 1.34 (3H, s), 1.53 (1H, m), 1.70-2.17 (5H, m), 2.54 (1H, d, J=14.4 Hz), 3.45 (1H, dq, J=1.9, 6.9 Hz), 3.65 (1H, dq, J=1.9, 6.9 Hz), 4.23 (1H, d, J=6.0 Hz), 4.25 (1H, d, J=11.1 HZ), 4.93 (1H, dq, J=2.1, 11.1 Hz), 5.37 (1H, br s).

Production Example 7

A colorless oily diastereomer mixture of (1C-2-4) and (1D-2-4) was obtained in a similar manner as in Production Example 5, except that n-butyl alcohol (16 ml) was used instead of benzyl alcohol. Next, the diastereomer mixture thus obtained was separated into the (1C-2-4) and (1D-2-4) shown below by normal-phase HPLC (Cosmosil 5SL-II Water (20×250), the ratio of n-hexane:ethyl acetate=6:1, 17.0 ml/min, detector: RI).

[Chem. 15]

(1C-2-4)

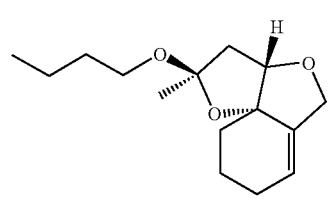

(1D-2-4)

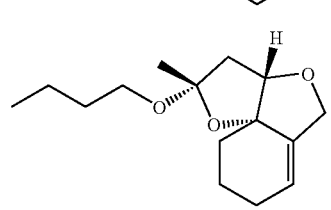

Physical Properties of Compound (1C-2-4):

$^1$H NMR (600 MHz in $C_6D_6$) δ ppm: 0.88 (3H, t, J=7.4 Hz), 1.13 (1H, ddd, J=3.0, 12.6, 13.8 Hz), 1.37 (2H, m), 1.50 (3H, s), 1.55-1.60 (3H, m), 1.72 (1H, m), 1.92 (2H, m), 2.18 (1H, dt, J=3.0, 12.6 Hz), 2.32 (1H, dd, J=1.4, 14.4 Hz), 2.44 (1H, dd, J=5.6, 14.4 Hz), 3.38 (1H, dt, J=6.3, 9.0 Hz), 3.62 (1H, dt, J=6.6, 9.0 Hz), 4.17 (1H, dd, J=1.9, 9.8 Hz), 4.19 (1H, dd, J=1.1, 5.4 Hz), 4.54 (1H, m), 5.30 (1H, br s)

$^{13}$C NMR (150 MHz in $C_6D_6$) δ ppm: 14.12q, 18.63t, 19.84t, 24.42q, 24.72t, 30.22t, 32.68t, 47.93t, 61.09t, 69.97t, 87.58s, 88.26d, 109.76s, 120.93d, 139.95s.

Physical Properties of Compound (1D-2-4):
$^1$H NMR (600 MHz in C$_6$D$_6$) δ ppm: 0.84 (3H, t, J=7.4 Hz), 1.16 (1H, ddd, J=3.6, 12.6, 14.4 Hz), 1.34 (2H, m), 1.36 (3H, s), 1.49-1.62 (3H, m), 1.71-1.80 (3H, m), 1.92 (1H, m), 2.00 (1H, m), 2.54 (1H, d, J=14.4 Hz), 3.44 (1H, dt, J=6.9, 9.0, Hz), 3.53 (1H, ddd, J=5.8, 7.2, 9.0 Hz), 4.20 (1H, d, J=5.6 Hz), 4.26 (1H, dd, J=1.6, 10.8 Hz), 4.92 (1H, ddt, J=2.2, 3.6, 10.8, Hz), 5.37 (1H, br s)
$^{13}$C NMR (150 MHz in C$_6$D$_6$) δ ppm: 14.14q, 18.50t, 19.85t, 24.59t, 24.81q, 32.25t, 32.69t, 47.49t, 61.49t, 70.70t, 87.56s, 88.03d, 108.48s, 120.95d, 140.47.

Production Example 8

A colorless oily diastereomer mixture of (1C-2-5) and (1D-2-5) was obtained in a similar manner as in Production Example 5, except that allyl alcohol (16 ml) was used instead of benzyl alcohol.

[Chem. 16]

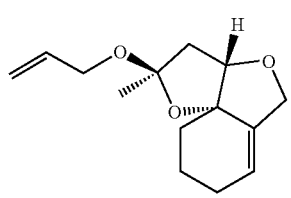
(1C-2-5)

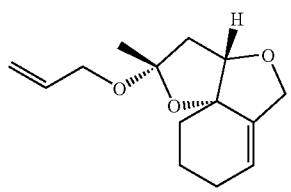
(1D-2-5)

Physical Properties of a Diastereomer Mixture of Compound (1C-2-5) and Compound (1D-2-5):
$^1$H NMR (300 MHz in C$_6$D$_6$) δ ppm: 1.23 (1H, dt, J=3.0, 13.2 Hz, major), 1.43 (3H, s, minor), 1.55 (3H, s, major), 1.60-2.01 (m), 2.29 (1H, dt, J=3.6, 12.9 Hz), 2.40 (1H, dd, J=1.5, 14.4 Hz), 2.59 (1H, dd, J=5.7, 14.4 Hz), 2.66 (1H, d, J=14.4 Hz), 4.01 (1H, ddt, J=1.8, 4.8, 12.9 Hz, major), 4.89 (1H, ddt, J=1.8, 4.8, 13.2 Hz, minor), 4.19-4.35 (m), 4.62 (1H, dq, J=3.0, 11.4 Hz), 5.00 (1H, dq, J=2.4, 11.1 Hz, minor), 5.14 (1H, dq, 1.8, 10.5 Hz, major), 5.34-5.46 (2H, m), 6.0 (1H, m).

Production Example 9

A colorless oily diastereomer mixture of (1C-2-6) and (1D-2-6) was obtained in a similar manner as in Production Example 5, except that prenyl alcohol (16 ml) was used instead of benzyl alcohol.

[Chem. 17]

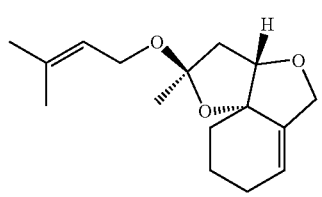
(1C-2-6)

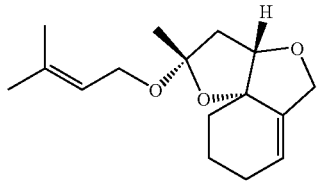
(1D-2-6)

Physical Properties of a Diastereomer Mixture of Compound (1C-2-6) and Compound (1D-2-6):
$^1$H NMR (200 MHz in C$_6$D$_6$) δ ppm: 1.15 (1H, dt, J=3.2, 12.8 Hz), 1.51 (3H, s), 1.54 (3H, s), 1.61 (3H, s), 1.7-2.0 (m), 2.26 (1H, dt, J=3.0, 13.0 Hz), 2.30 (1H, dd, J=1.6, 14.0 Hz), 2.51 (1H, dd, J=5.6, 14.0 Hz), 4.03 (1H, dd, J=6.6, 11.2 Hz), 4.12-4.29 (m), 4.53 (1H, dq, J=3.0, 11.4 Hz), 5.33 (1H, br s), 5.49 (1H, br t, J=6.8 Hz).

Production Example 10

A colorless oily diastereomer mixture of (1C-2-7) and (1D-2-7) was obtained in a similar manner as in Production Example 5, except that cinnamyl alcohol (16 ml) was used instead of benzyl alcohol.

[Chem. 18]

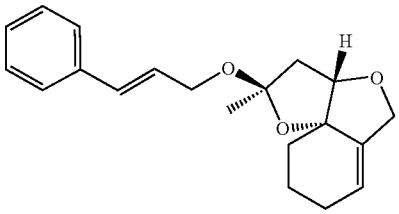
(1C-2-7)

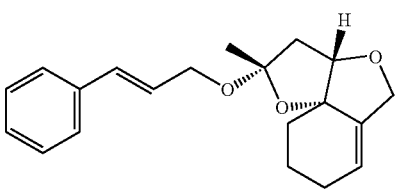
(1D-2-7)

Physical Properties of a Diastereomer Mixture of Compound (1C-2-7) and Compound (1D-2-7):
$^1$H NMR (200 MHz in C$_6$D$_6$) δ ppm: 1.15 (1H, m), 1.28-2.05 (m), 1.39 (3H, s, minor), 1.52 (3H, s, major), 2.25(1H, dt, J=3.0, 13.0 Hz), 2.34 (1H, dd, J=1.6, 14.4 Hz), 2.54 (1H, dd, J=5.8, 14.4 Hz), 2.61 (1H, d, J=14.4 Hz), 4.02-4.37 (m), 4.55 (1H, dq, J=3.0, 11.4 Hz, major), 4.95 (1H, dq, J=3.0, 11.0 Hz, minor), 5.33 (1H, br s), 6.27 (1H, dt, J=5.4, 16.0 Hz, major), 6.29 (1H, dt, J=5.4, 15.8 Hz, minor), 6.62 (1H, br d, J=16.0 Hz, major), 6.66 (1H, dt, J=1.8, 16.0 Hz, minor), 6.99-7.16 (m), 7.26 (2H, dt, J=1.4, 6.2 Hz).

Test Example

Preparation of Medium and Reagent
Preparation of Dulbecco's Modified Eagle Medium (DMEM)/10% HS, 5% FBS
Donor horse serum (HS) (5 ml), fetal bovine serum (FBS) (2.5 ml), and penicillin-streptomycin (0.5 ml) were added to DMEM (total amount: 50 ml), and thereby DMEM/10% HS, 5% FBS were prepared.

Preparation of DMEM/2% HS, 1% FBS

HS (1 ml), FBS (0.5 ml) and penicillin-streptomycin (0.5 ml) were added to DMEM (total amount: 50 ml), and thereby DMEM/2% HS, 1% FBS was prepared.

Preparation of 0.25% trypsin/PBS (Phosphate Buffered Saline)

2.5% trypsin was diluted 10-fold with PBS, and thereby 0.25% trypsin/PBS was prepared.

Preparation of 0.4% Trypan Blue 0.4% trypan blue was prepared by dissolving 0.2 g of trypan blue in 50 ml PBS.

Preparation of Sample

When the solvent was ethanol, the concentrations were targeted at 1 mM, 0.1 mM, and 10 mM. A sample at 1 mM concentration was prepared first. When the amount of sample was 1 mg, the sample was dissolved in 100% ethanol (1/molecular weight×1,000)/2 ml, and an equal amount of Milli-Q (1/molecular weight×1,000)/2 ml was added thereto, after which the sample was filtered through a 0.45 mM filter into a sample tube.

A sample at 0.1 mM concentration was prepared by diluting 1 mM solution 10-fold with 50% ethanol. Likewise, a sample at 10 mM concentration was prepared from 0.1 mM solution.

When the solvent was DMSO, the concentrations were targeted at 10 mM, 1 mM, and 0.1 mM.

When the sample is prepared in ethanol, the sample is diluted 100-fold with the medium; and when the sample is prepared in DMSO, the sample is diluted 1,000-fold in the medium. The actual concentrations of the sample were thus 10 mM, 1 mM, and 0.1 mM both when the sample was prepared in ethanol and when the sample was prepared in DMSO.

Neurite Outgrowth Measuring Method

Measurement was carried out using the following equipment and software.

Research-level inverted microscope 1×70 (Olympus Corporation)

High-resolution CCD cooled digital color camera C4742-95-12SC (Hamamatsu Photonics K.K.)

Lumina Vision fluorescence imaging analysis system and MacSCOPE image analysis package (Mitani Corporation)

Statistical Processing

Statistical processing of obtained data was carried out using "Origin ver. 7.0" (OriginLab, USA) and Mac Statistical Analysis. The significant difference was determined using Student's T-test and Dunnett's T-test.

Experimental Test Material and Reagent

Cell

Pheochromocytoma (PC12) cells were purchased from the Health Science Research Resources Bank of the Japan Health Sciences Foundation. Cell number: JCRB0733, product name: PC-12.

Reagents

DMEM, penicillin-streptomycin, HS, FBS, trypsin, and nerve growth factor (NGF) were obtained from GIBCOBAL. DULBECCO'S PBS was obtained from Dainippon Pharma Co., Ltd. Ethanol and dimethyl sulfoxide (DMSO) were obtained from Nacalai Tesque, Inc.

Experimental Test Method

Cell Culture

PC12 cells were cultivated in a medium having a composition including DMEM/10% HS, 5% FBS, 50 IU/ml penicillin, and 50 mg/ml streptomycin, in a culture flask coated with rat tail-derived collagen, in an incubator (95% humidity, 5% carbon dioxide). When the cell density becomes obviously too low, or when the cells overproliferate, the cells would be under load, requiring a longer time for proliferation and/or causing the cells to dye out. Thus, the cells were subcultured such that the cells would be present at a density of about 80% in the flask. When cells were subcultured or when activity evaluation tests were carried out, the cells were treated with trypsin (0.25%, 5 min.) to obtain a cell suspension, which was then seeded into a collagen-coated culture flask or plate.

Cell Isolation and Seeding

The condition of the PC12 cells was observed; it was confirmed that at least 50% of the PC12 cells were fused. The plate was coated with rat tail-derived collagen; on the following day, the plate was washed twice with Milli-Q water. Then, a medium having a composition including DMEM/10% HS, 5% FBS, 50 IU/ml penicillin, and 50 mg/ml streptomycin was prepared.

The medium in the culture flask was removed by suction. The PC12 cells were washed twice with PBS (5 mL), and trypsin (3 mL) was added thereto, which was then left to stand for about 5 minutes. A cell suspension was obtained by pipetting. In order to inhibit the activity of the trypsin, the cell suspension was transferred to a 50 mL centrifuge tube containing a serum-containing medium (2 mL). The total amount was adjusted to 10 mL with PBS, and the cell suspension was centrifuged (1,000 rpm×5 min). After centrifuging, the supernatant liquid was removed by suction using a pump, PBS (10 mL) was added thereto, and pipetting was carried out several times using a bent-tip Komagome pipette. After pipetting, the cell suspension was centrifuged again, and a similar operation was repeated twice. After the second centrifuging, the prepared medium (5 mL) was added to the tube, pipetting was carried out several times using a bent-tip Komagome pipette, and a cell suspension was thereby obtained.

Screening Method

The cells were isolated by the method described above, and seeded into a 48-well plate such that the cell density was 2,000 cells/cm$^2$ in the medium having a composition including DMEM/10% HS, 5% FBS. After the cells were cultured for 24 hours in an incubator, the medium was exchanged with a sample-containing medium including DMEM/2% HS, 1% FBS and NGF (10 ng/ml) as well as a medium including DMEM/2% HS, 1% FBS and NGF (10 ng/ml). Cell culturing continued in the incubator, and the cell form was observed under a microscope for one week from the day following the medium exchange. During this period, when neurite outgrowth was observed, the neurite outgrowth was photographed using a digital camera.

The sample was prepared using 50% ethanol and DMSO. The sample prepared using 50% ethanol was diluted 100-fold in the medium, and the sample prepared using DMSO was diluted 1,000-fold in the medium.

Judgment on Neurite Outgrowth Activity

As for the determination of neurite outgrowth activity, when a cell with at least one neurite longer than the cell body was observed, the cell was counted as a neurite formation. The neurite length was determined by a comparison between the control (50% ethanol or 0.1% DMSO), and cells that underwent differentiation induced by adding NGF (10 ng/ml).

Activity Test Result

[Chem. 19]

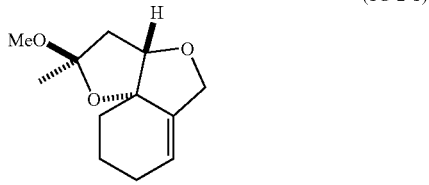
(1C-2-1)

Figure 2:
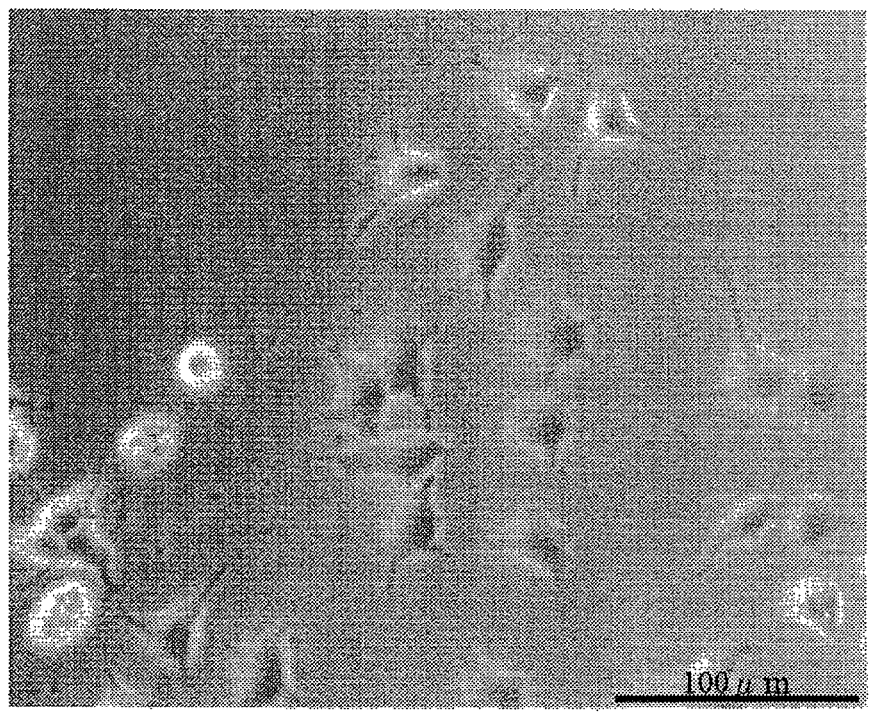
FIG. 2 is a micrograph showing cells cultivated in a medium containing DMSO and NGF (20 ng/ml).
Figure 3:
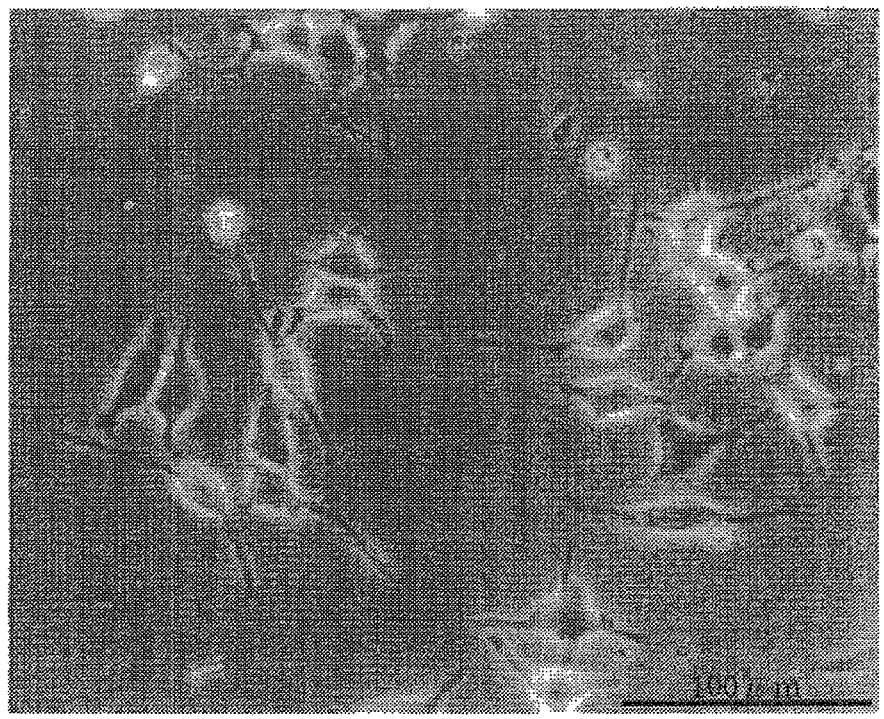
FIG. 3 is a micrograph showing cells cultivated in a medium containing DMSO, NGF (20 ng/ml), and bis(tetrahydrofuran) compound (1C-2-1) (1 μM) of the present invention.
Figure 4:
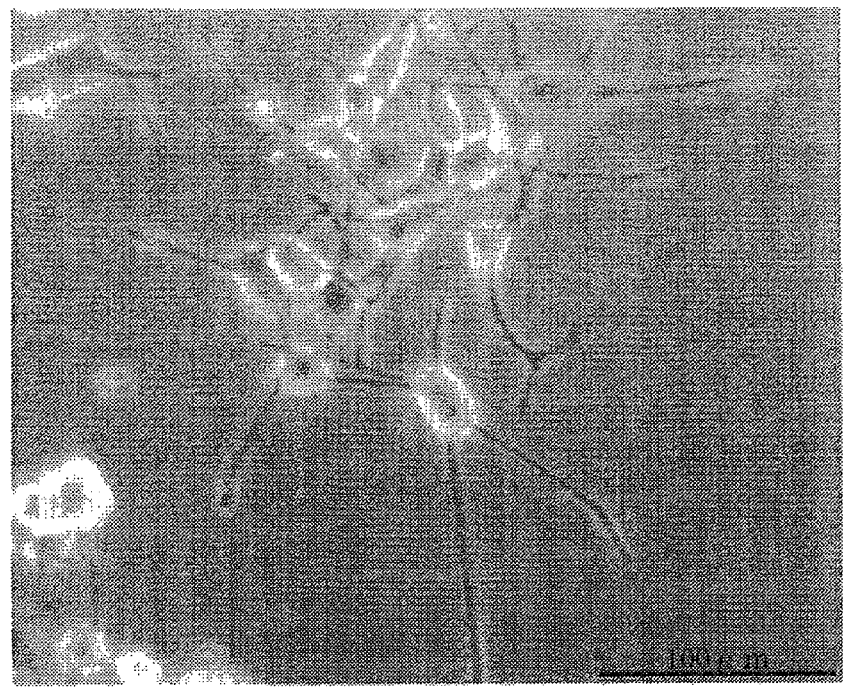
FIG. 4 is a micrograph showing cells cultivated in a medium containing DMSO, NGF (20 ng/ml), and bis(tetrahydrofuran) compound (1C-2-1) (10 μM) of the present invention.

FIG. 1 is a micrograph showing cells cultivated in a medium containing DMSO. FIG. 2 is a micrograph showing cells cultivated in a medium containing DMSO and NGF (20 ng/ml). FIG. 3 is a micrograph showing cells cultivated in a medium containing DMSO, NGF (20 ng/ml), and compound (1C-2-1) (1 μM). FIG. 4 is a micrograph showing cells cultivated in a medium containing DMSO, NGF (20 ng/ml), and compound (1C-2-1) (10 μM). As is clear from FIGS. 3 and 4, under the presence of DMSO and NGF (20 ng/ml), the sample including 1 μM or 10 μM of compound (1C-2-1) resulted in further enhanced neurite outgrowth activity, compared with the sample without compound (1C-2-1).

[Chem. 20]

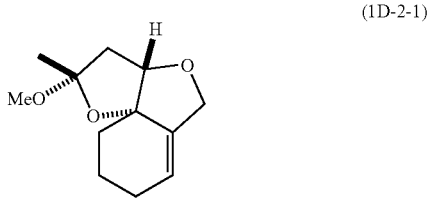
(1D-2-1)

Figure 5:
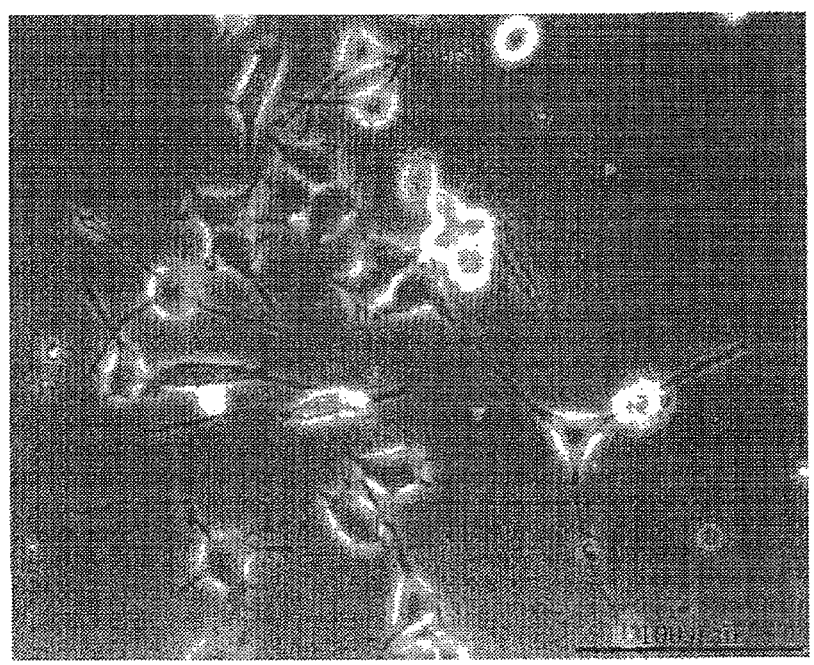
FIG. 5 is a micrograph showing cells cultivated in a medium containing DMSO, NGF (20 ng/ml), and bis(tetrahydrofuran) compound (1D-2-1) (1 μM) of the present invention.
Figure 6:
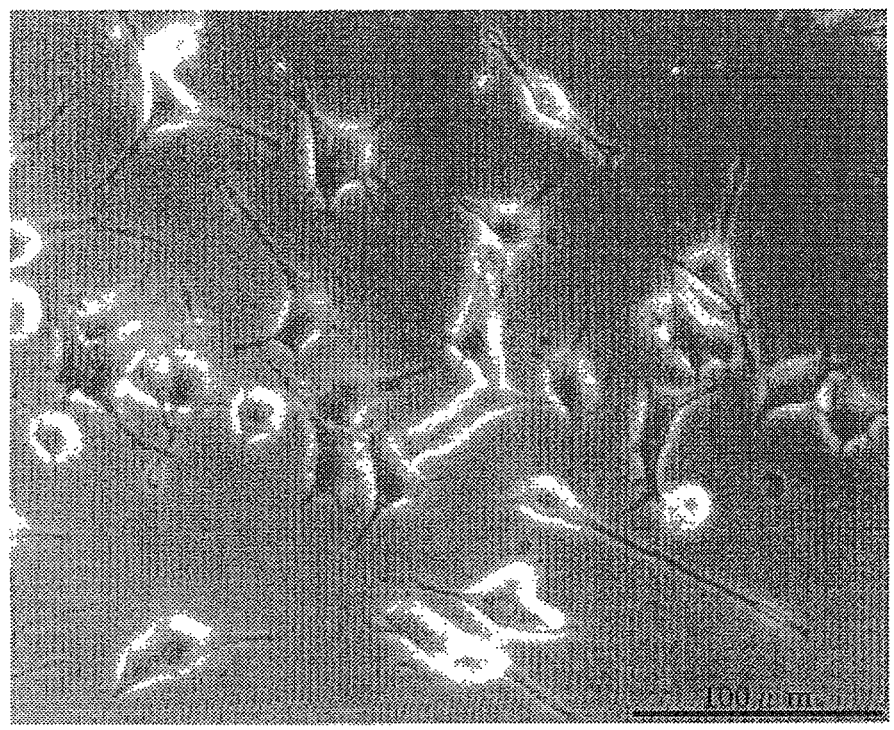
FIG. 6 is a micrograph showing cells cultivated in a medium containing DMSO, NGF (20 ng/ml), and bis(tetrahydrofuran) compound (1D-2-1) (10 μM) of the present invention.

FIG. 5 is a micrograph showing cells cultivated in a medium containing DMSO, NGF (20 ng/ml), and compound (1D-2-1) (1 μM). FIG. 6 is a micrograph showing cells cultivated in a medium containing DMSO, NGF (20 ng/ml), and compound (1D-2-1) (10 μM). As is clear from FIGS. 5 and 6, under the presence of DMSO and NGF (20 ng/ml), the sample including 1 μM or 10 μM of compound (1D-2-1) resulted in further enhanced neurite outgrowth activity, compared with the sample without compound (1D-2-1).

Compound (1D-2-3) and the diastereomer mixture of compound (1C-2-5) and compound (1D-2-5) were also subjected to the activity test in a manner similar to that described above. The results show that, under the presence of DMSO and NGF (20 ng/ml), the sample including 10 μM of compound (1D-2-3) resulted in further enhanced neurite outgrowth activity, compared with the sample without compound (1D-2-3). The results also show that, under the presence of DMSO and NGF (20 ng/ml), the sample including 10 μM of the diastereomer mixture of compound (1C-2-5) and compound (1D-2-5) resulted in further enhanced neurite outgrowth activity, compared with the sample without the diastereomer mixture of compound (1C-2-5) and compound (1D-2-5).

The invention claimed is:

1. A bis(tetrahydrofuran) compound represented by the following formula (1):

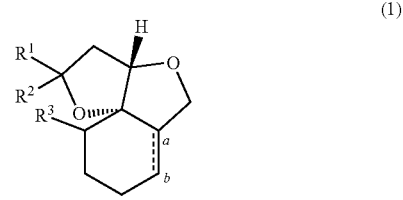
(1)

wherein $R^1$ and $R^2$ are the same or different, and represent a $C_{1-4}$ alkyl group, a $C_{1-5}$ alkoxy group, an aryl $C_{1-5}$ alkoxy group, a $C_{2-5}$ alkenyloxy group, or an aryl $C_{2-5}$ alkenyloxy group, or $R^1$ and $R^2$ together represent =O or =CH$_2$; $R^3$ represents a hydrogen atom or a group —CH$_2$—O—R$^4$; R$^4$ represents a $C_{1-4}$ alkyl group, a $C_{1-5}$ alkylcarbonyl group, or an aryl $C_{1-4}$ alkyl group optionally having one or more substituents on the aryl ring; and a carbon-carbon bond between "a" and "b" represents a single bond or a double bond.

2. The bis(tetrahydrofuran) compound according to claim 1, wherein $R^1$ and $R^2$ together represent =O in formula (1).

3. The bis(tetrahydrofuran) compound according to claim 1, wherein $R^1$ and $R^2$ together represent =CH$_2$ in formula (1).

4. The bis(tetrahydrofuran) compound according to claim 1, wherein $R^1$ represents a $C_{1-4}$ alkyl group, and $R^2$ represents a $C_{1-5}$ alkoxy group, an aryl $C_{1-5}$ alkoxy group, a $C_{2-5}$ alkenyloxy group, or an aryl $C_{2-5}$ alkenyloxy group.

5. A process for producing the bis(tetrahydrofuran) compound of claim 2, comprising reacting an acrylic acid compound represented by the following formula (2) with a quaternary ammonium fluoride:

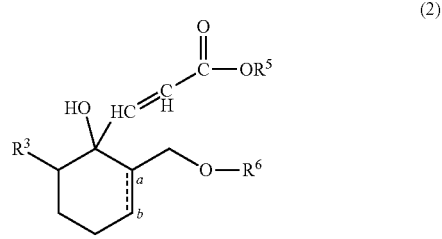
(2)

wherein $R^3$ and a carbon-carbon bond between "a" and "b" are as defined above; $R^5$ represents a $C_{1-4}$ alkyl group; and $R^6$ represents a silyl-based protecting group.

6. A process for producing bis(tetrahydrofuran) compound represented by the following formula (1):

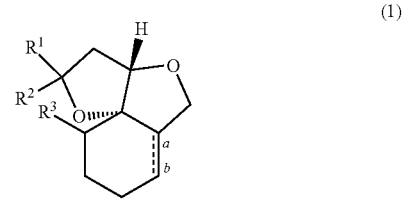
(1)

wherein $R^1$ and $R^2$ are together represent =CH$_2$; $R^3$ represents a hydrogen atom or a group —CH$_2$—O—R$^4$; R$^4$ represents a $C_{1-4}$ alkyl group, a $C_{1-5}$ alkylcarbonyl group, or an aryl $C_{1-4}$ alkyl group optionally having one or more substituents on the aryl ring; and a carbon-carbon bond between "a" and "b" represents a single bond or a double bond, comprising reacting the bis(tetrahydrofuran) compound of claim 2 with Tebbe's reagent.

7. A process for producing bis(tetrahydrofuran) compound represented by the following formula (1):

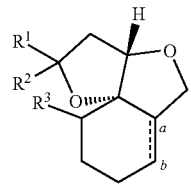

wherein $R^1$ represents a $C_{1-4}$ alkyl group, and $R^2$ represents a $C_{1-5}$ alkoxy group, an aryl $C_{1-5}$ alkoxy group, a $C_{2-5}$ alkenyloxy group, or an aryl $C_{1-5}$ alkoxy group, a $C_{2-5}$ alkenyloxy group, or an aryl $C_{2-5}$ alkenyloxy group; $R^3$ represents a hydrogen atom or a group —$CH_2$—O—$R^4$; $R^4$ represents a $C_{1-4}$ alkyl group, a $C_{1-5}$ alkylcarbonyl group, or an aryl $C_{1-4}$ alkyl group optionally having one or more substituents on the aryl ring; and a carbon-carbon bond between "a" and "b" represents a single bond or a double bond, comprising reacting the bis(tetrahydrofuran) compound of claim 3 in an alcohol in the presence of an acid catalyst.

8. A pharmaceutical composition, comprising:
the bis(tetrahydrofuran) compound of claim 1; and
a carrier or an additive.

* * * * *